US007253008B2

(12) United States Patent
Rucker et al.

(10) Patent No.: US 7,253,008 B2
(45) Date of Patent: Aug. 7, 2007

(54) REACTIVE ION ETCHED SUBSTRATES AND METHODS OF MAKING AND USING

(75) Inventors: Victor C. Rucker, San Francisco, CA (US); Renée Shediac, Oakland, CA (US); Blake A. Simmons, San Francisco, CA (US); Karen L. Havenstrite, New York, NY (US)

(73) Assignee: Sandia Corporation, Albuquerque, NM (US)

( * ) Notice: Subject to any disclaimer, the term of this patent is extended or adjusted under 35 U.S.C. 154(b) by 231 days.

(21) Appl. No.: 11/022,862

(22) Filed: Dec. 28, 2004

(65) Prior Publication Data

US 2006/0141484 A1 Jun. 29, 2006

(51) Int. Cl.
G01N 33/566 (2006.01)
G01N 33/00 (2006.01)
C12M 3/00 (2006.01)
C07K 1/00 (2006.01)
C07K 16/00 (2006.01)

(52) U.S. Cl. ............... 436/501; 436/94; 435/287.2; 435/810; 530/350; 530/387.1
(58) Field of Classification Search ............... 436/501, 436/94; 435/287.2, 6; 530/350
See application file for complete search history.

(56) References Cited

U.S. PATENT DOCUMENTS 5,217,492 A * 6/1993 Guire et al. ............... 600/36
6,495,320 B1 * 12/2002 Lockhart et al. ............ 435/6
6,719,896 B1 * 4/2004 Clark ........................ 210/91
7,115,305 B2 * 10/2006 Bronikowski et al. ... 427/249.1

* cited by examiner

Primary Examiner—Bradley L. Sisson
(74) Attorney, Agent, or Firm—Suzannah K. Sundby, Esq.; Smith, Gambrell & Russell, LLP

(57) ABSTRACT

Disclosed herein are substrates comprising reactive ion etched surfaces and specific binding agents immobilized thereon. The substrates may be used in methods and devices for assaying or isolating analytes in a sample. Also disclosed are methods of making the reactive ion etched surfaces.

13 Claims, 11 Drawing Sheets

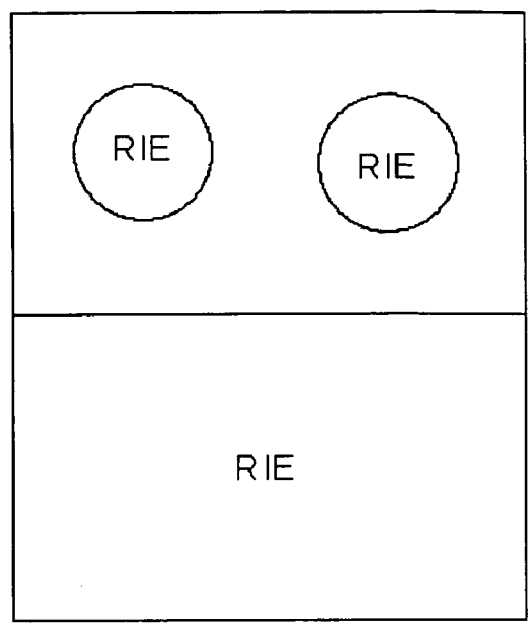
Figure 2A1
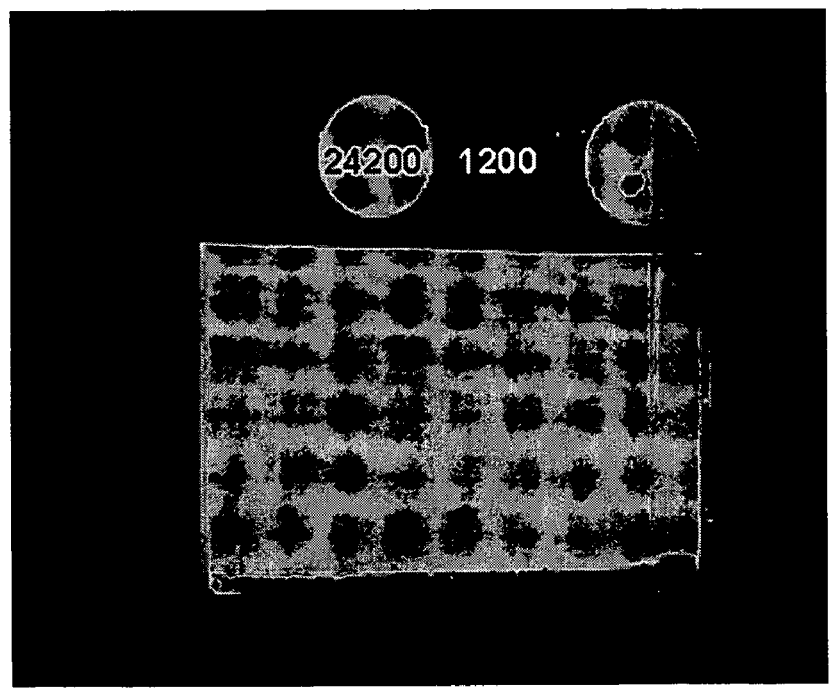
Figure 2A2

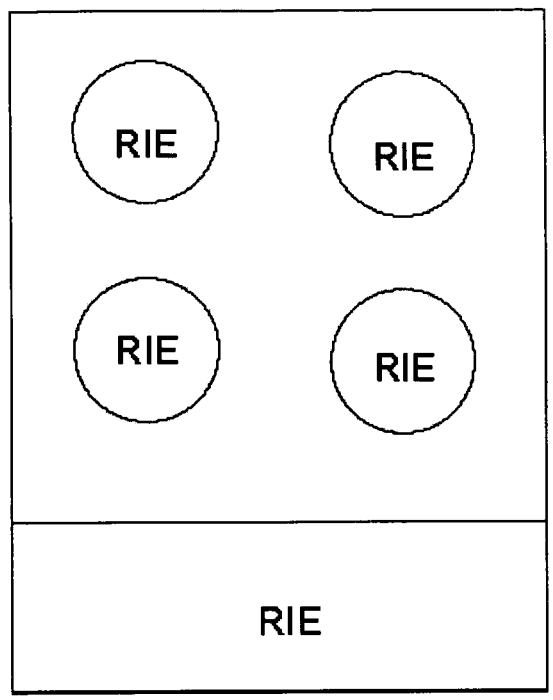
Figure 2B1
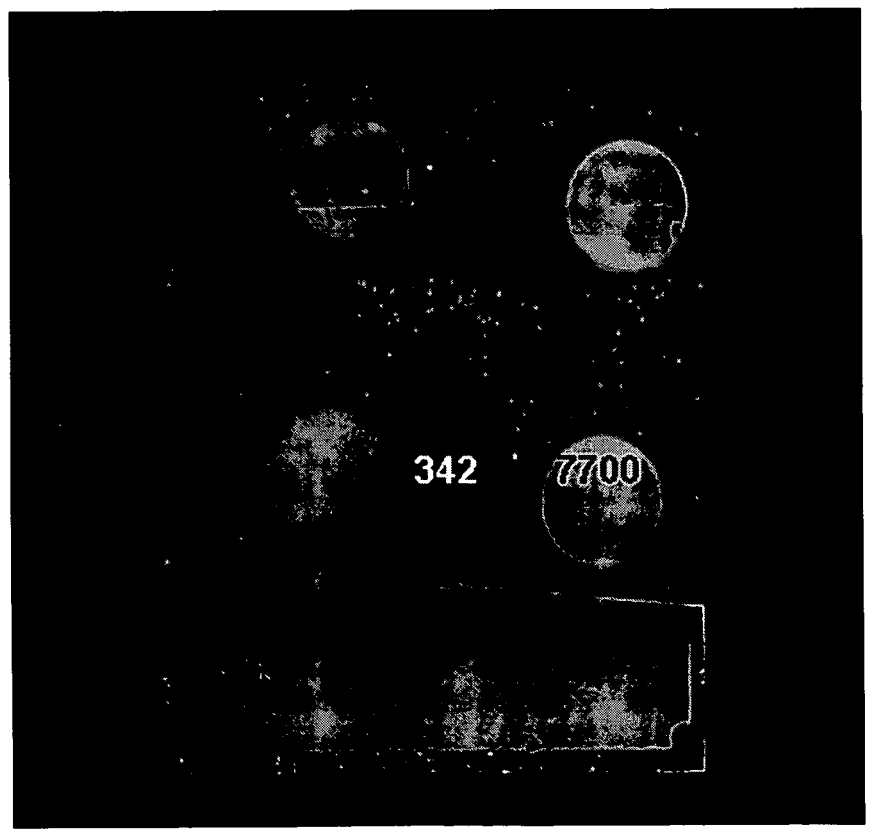
Figure 2B2

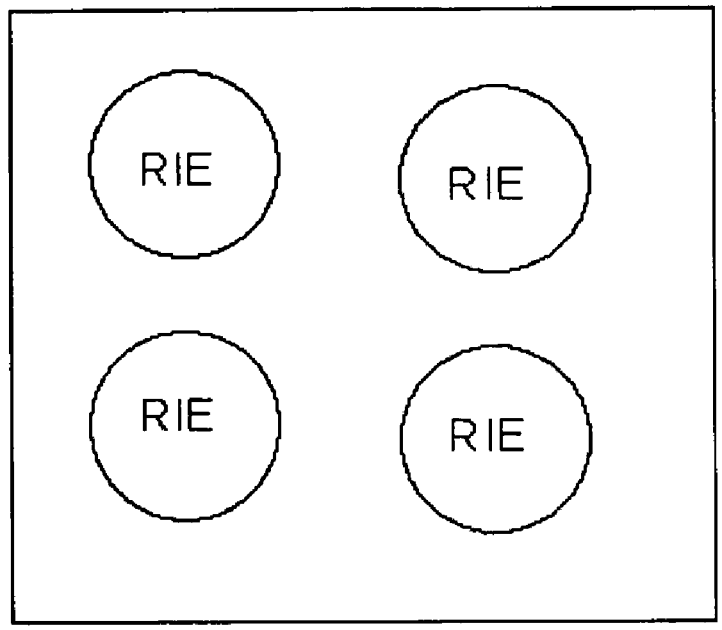
Figure 2C1
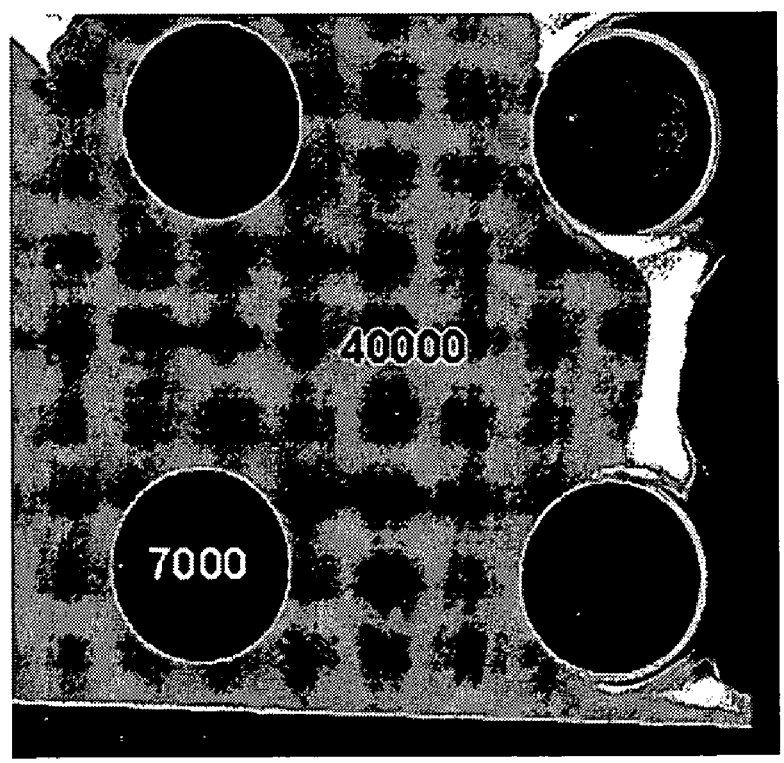
Figure 2C2

α-SEB + SEB
Figure 5A

α-SEB + DT
Figure 5B

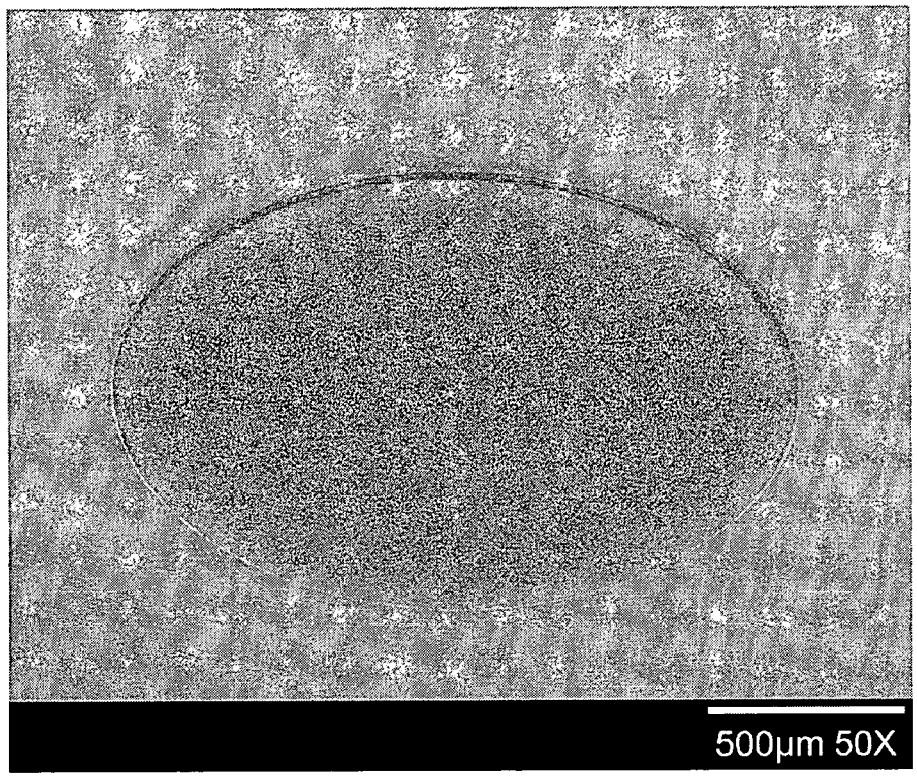
Figure 6A1
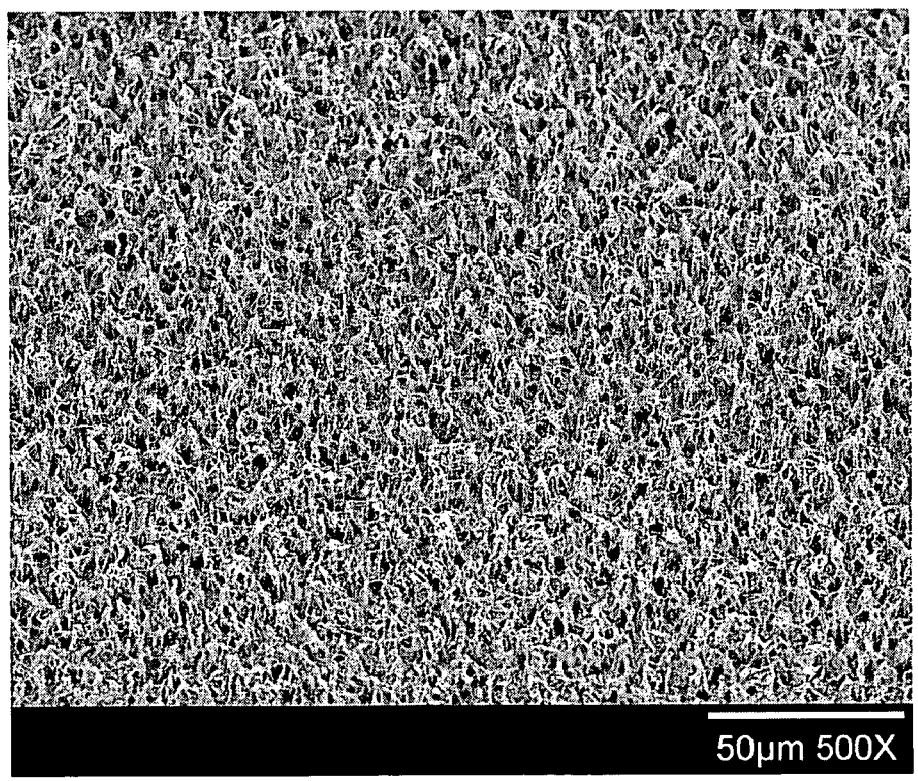
Figure 6A2

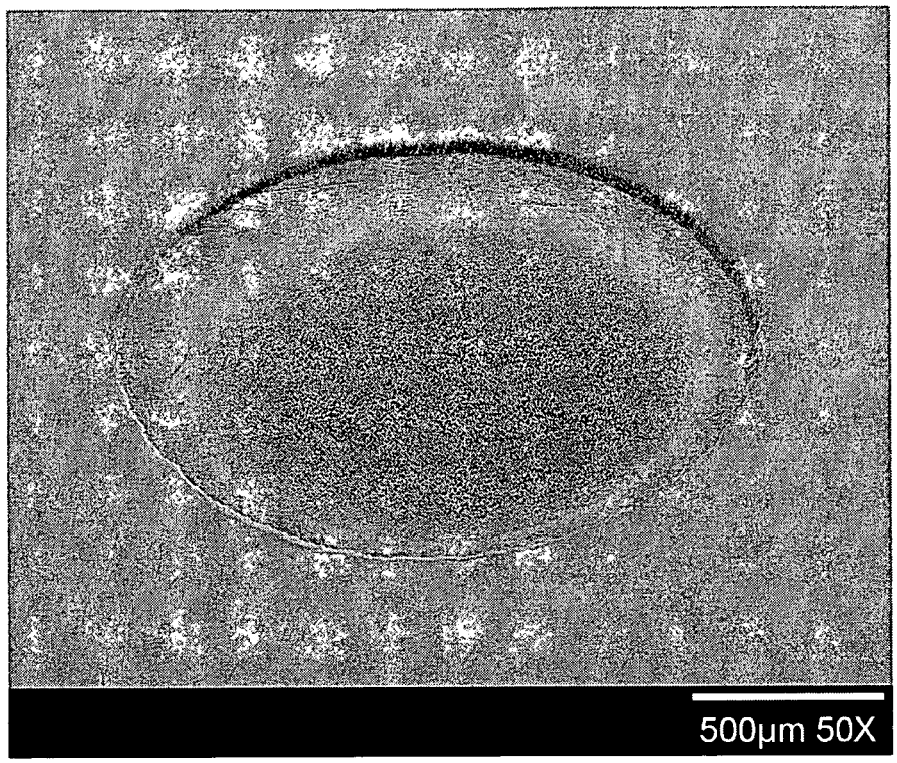
Figure 6B1
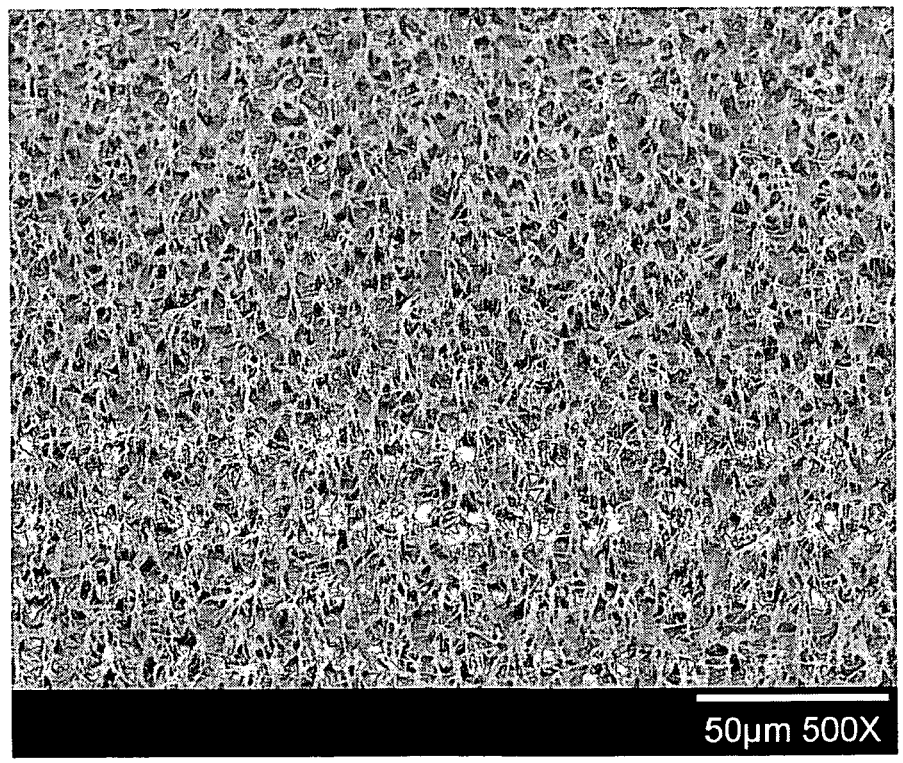
Figure 6B2

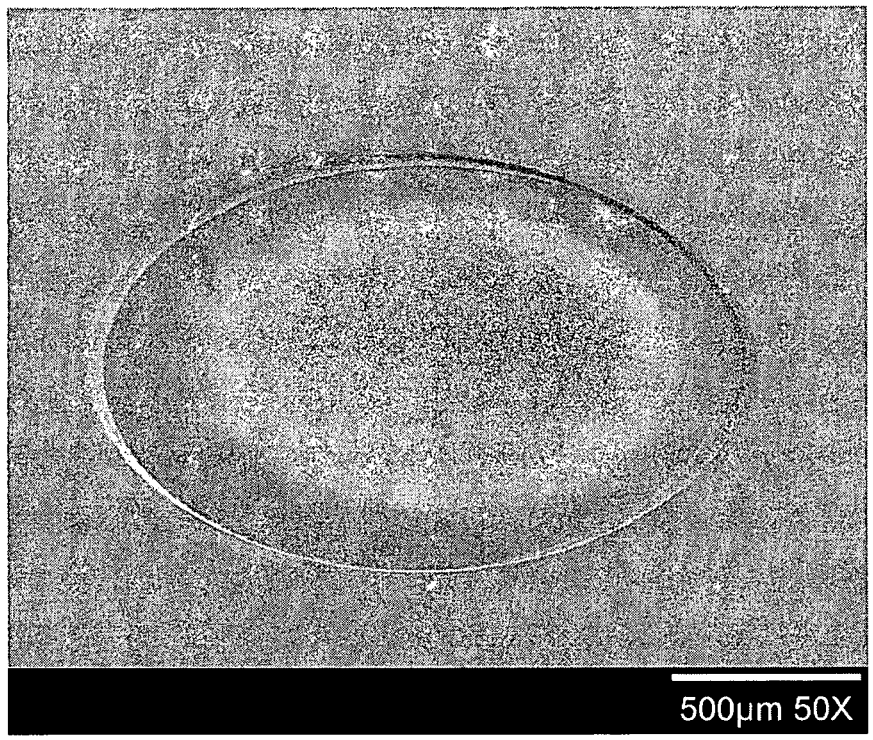
Figure 6C1
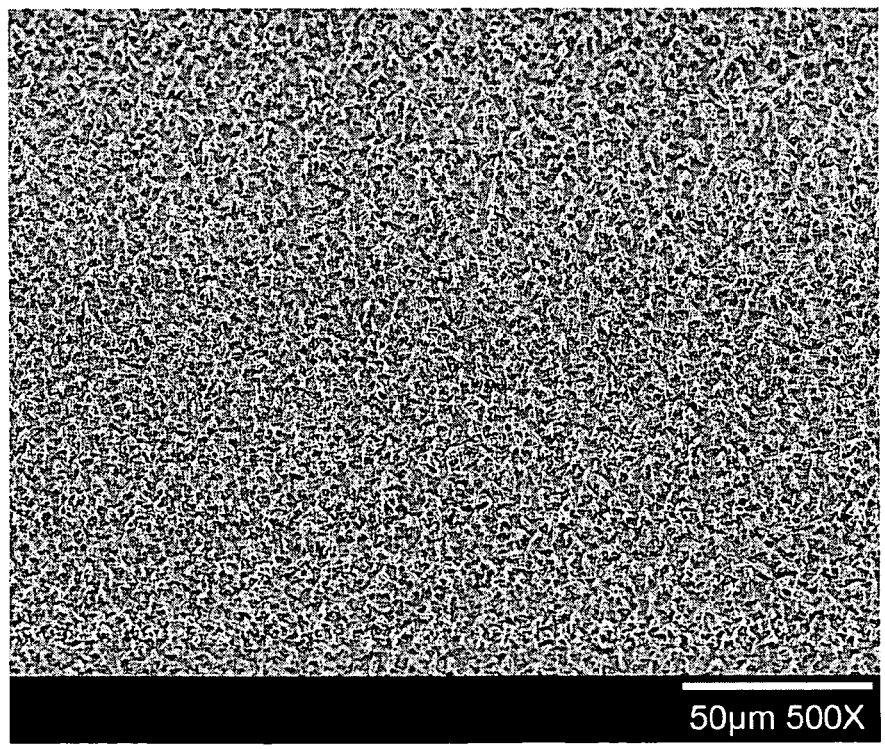
Figure 6C2

REACTIVE ION ETCHED SUBSTRATES AND METHODS OF MAKING AND USING

ACKNOWLEDGMENT OF GOVERNMENT SUPPORT

Employees of Sandia National Laboratories made this invention. The government has rights in the invention.

BACKGROUND OF THE INVENTION

1. Field of the Invention

The present invention generally relates to reactive ion etched polymer surfaces and methods of using in various chemical and biological assays.

2. Description of the Related Art

Optimizing surface chemistry to enable immobilization of detection antibodies while retaining bioactivity and minimizing non-specific protein adsorption remains a challenge in the development of robust diagnostic protein microarrays for rapid, high throughput screening of pathogen and toxin exposure. Non-specific protein binding greatly compromises assay sensitivity, so minimizing non-specific adsorption and maximizing the binding ability of antibodies will improve detection limits. Most immobilization strategies developed for protein microarrays involve covalent attachment or non-covalent affinity binding of proteins on glass surfaces, followed by a bovine serum albumin (BSA) blocking step to suppress non-specific binding. Because glass-based microarrays are limited in sensitivity and are particularly susceptible to non-specific background binding, other solid support materials are currently being developed for protein microarray applications. The ideal support surface should provide reasonably strong signals, good signal-to-noise ratios, and an almost negligible background.

Polymers possess desirable bulk physical and chemical properties and are inexpensive and easy to process. However, polymers characteristically exhibit low surface energy and must therefore be modified before use in most applications.

Thus, a need exists for polymer substrates that are suitable for patterned microarrays for high-thoughput assays.

SUMMARY OF THE INVENTION

The present invention generally relates to assay devices containing substrates having reactive ion etched polymer surfaces.

In some embodiments, the present invention provides a substrate containing at least one polymer having at least one reactive ion etched surface upon which at least one specific binding agent is immobilized. In some embodiments, the polymer has at least one unetched surface. In some embodiments, the unetched surface lacks a detectable specific binding agent immobilized thereon. In some embodiments, the unetched surface has at least one specific binding agent immobilized thereon which may be the same or different from the specific binding agent immobilized on the reactive ion etched surface. In some embodiments, the substrate contains two or more polymers each having at least one surface and wherein each surface is independently a reactive ion etched surface or an unetched surface. In some embodiments, the reactive ion etched surfaces each independently have at least one specific binding agent immobilized thereon which may be the same or different. In some embodiments, the unetched surfaces each independently have at least one specific binding agent which may be the same or different immobilized thereon or lack a detectable specific binding agent immobilized thereon. In some embodiments, the reactive ion etched surface is in a pattern on the substrate. In some embodiments, the unetched surface is in a pattern on the substrate. In some embodiments, the polymers are in a pattern. In some embodiments, the polymer is polycarbonate (PC), polymethylmethacrylate (PMMA), cyclo-olefin, or polyetherimide (PEI).

In some embodiments, the present invention provides an assay device comprising a substrate containing at least one polymer having at least one reactive ion etched surface upon which at least one specific binding agent is immobilized. In some embodiments, the polymer has at least one unetched surface. In some embodiments, the unetched surface lacks a detectable specific binding agent immobilized thereon. In some embodiments, the unetched surface has at least one specific binding agent immobilized thereon which may be the same or different from the specific binding agent immobilized on the reactive ion etched surface. In some embodiments, the substrate contains two or more polymers each having at least one surface and wherein each surface is independently a reactive ion etched surface or an unetched surface. In some embodiments, the reactive ion etched surfaces each independently have at least one specific binding agent immobilized thereon which may be the same or different. In some embodiments, the unetched surfaces each independently have at least one specific binding agent which may be the same or different immobilized thereon or lack a detectable specific binding agent immobilized thereon. In some embodiments, the reactive ion etched surface is in a pattern on the substrate. In some embodiments, the unetched surface is in a pattern on the substrate. In some embodiments, polymers are in a desired pattern. In some embodiments, the polymer is polycarbonate (PC), polymethylmethacrylate (PMMA), cyclo-olefin, or polyetherimide (PEI).

In some embodiments, the present invention provides a method of assaying or isolating a ligand in a sample comprising using a substrate containing at least one polymer having at least one reactive ion etched surface upon which at least one specific binding agent is immobilized. In some embodiments, the polymer has at least one unetched surface. In some embodiments, the unetched surface lacks a detectable specific binding agent immobilized thereon. In some embodiments, the unetched surface has at least one specific binding agent immobilized thereon which may be the same or different from the specific binding agent immobilized on the reactive ion etched surface. In some embodiments, the substrate contains two or more polymers each having at least one surface and wherein each surface is independently a reactive ion etched surface or an unetched surface. In some embodiments, the reactive ion etched surfaces each independently have at least one specific binding agent immobilized thereon which may be the same or different. In some embodiments, the unetched surfaces each independently have at least one specific binding agent which may be the same or different immobilized thereon or lack a detectable specific binding agent immobilized thereon. In some embodiments, the reactive ion etched surface is in a pattern on the substrate. In some embodiments, the unetched surface is in a pattern on the substrate. In some embodiments, the polymers are in a pattern. In some embodiments, the polymer is polycarbonate (PC), polymethylmethacrylate (PMMA), cyclo-olefin, or polyetherimide (PEI). In some embodiments, the specific binding agent is contacted with the sample. In some embodiments, the specific binding agent specifically binds the ligand.

In some embodiments, the present invention provides a kit comprising a substrate containing at least one polymer having at least one reactive ion etched surface upon which at least one specific binding agent is immobilized packaged together with reagents for assaying or isolating a ligand in a sample. In some embodiments, the polymer has at least one unetched surface. In some embodiments, the unetched surface lacks a detectable specific binding agent immobilized thereon. In some embodiments, the unetched surface has at least one specific binding agent immobilized thereon which may be the same or different from the specific binding agent immobilized on the reactive ion etched surface. In some embodiments, the substrate contains two or more polymers each having at least one surface and wherein each surface is independently a reactive ion etched surface or an unetched surface. In some embodiments, the reactive ion etched surfaces each independently have at least one specific binding agent immobilized thereon which may be the same or different. In some embodiments, the unetched surfaces each independently have at least one specific binding agent which may be the same or different immobilized thereon or lack a detectable specific binding agent immobilized thereon. In some embodiments, the reactive ion etched surface is in a pattern on the substrate. In some embodiments, the unetched surface is in a pattern on the substrate. In some embodiments, the polymers are in a pattern. In some embodiments, the polymer is polycarbonate (PC), polymethylmethacrylate (PMMA), cyclo-olefin, or polyetherimide (PEI). The reagents are those known in the art for use in various assays and include buffers, tags, and the like.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 2A1 shows a schematic of etched and unetched areas on PMMA substrate.

FIG. 2A2 shows fluorescent signal and observed background for application of IgG-Cy3 at about 1 mg/ml to PMMA substrate. Note lack of signal from unetched areas.

FIG. 2B1 shows a schematic of etched and unetched areas on Zeonex® substrate.

FIG. 2B2 shows fluorescent signal and observed background for application of IgG-Cy3 at about 1 mg/ml to Zeonex® substrate. Note lack of signal from unetched areas.

FIG. 2C1 shows a schematic of etched and unetched areas on PC substrate.

FIG. 2C2 shows fluorescent signal and observed background for application of IgG-Cy3 at about 1 mg/ml to PC substrate. Note lack of signal from etched areas.

FIG. 4A shows Zeonex® substrate patterned with α-cholera toxin (α-CT) monoclonal antibody. Fluorescence was observed post addition of fluorescent (cholera toxin) CT due to specific antibody-antigen interaction.

FIG. 4B shows Zeonex® substrate patterned with α-CT. Lack of fluorescent signal post addition of fluorescent protective antigen (PA).

FIG. 5A shows PMMA substrate patterned with α-*Staphylococcus* enterotoxin B (α-SEB) monoclonal antibody. Fluorescence was observed post addition of fluorescent SEB due to specific antibody-antigen interaction.

FIG. 5B shows PMMA substrate patterned with α-SEB. Lack of fluorescent signal post addition of fluorescent diphtheria toxin (DT).

FIG. 6A1 shows an SEM micrograph of about a 25 μm deep etched hole in PMMA.

FIG. 6A2 shows an SEM image showing roughened etched PMMA surface.

FIG. 6B1 shows an SEM micrograph of about a 30 μm deep etched hole in Zeonex®.

FIG. 6B2 shows an SEM image showing roughened etched Zeonex® surface.

FIG. 6C1 shows an SEM micrograph of about a 25 μm deep etched hole in PC.

FIG. 6C2 shows an SEM image showing roughened etched PC surface.

DETAILED DESCRIPTION OF THE INVENTION

Figure 1A:
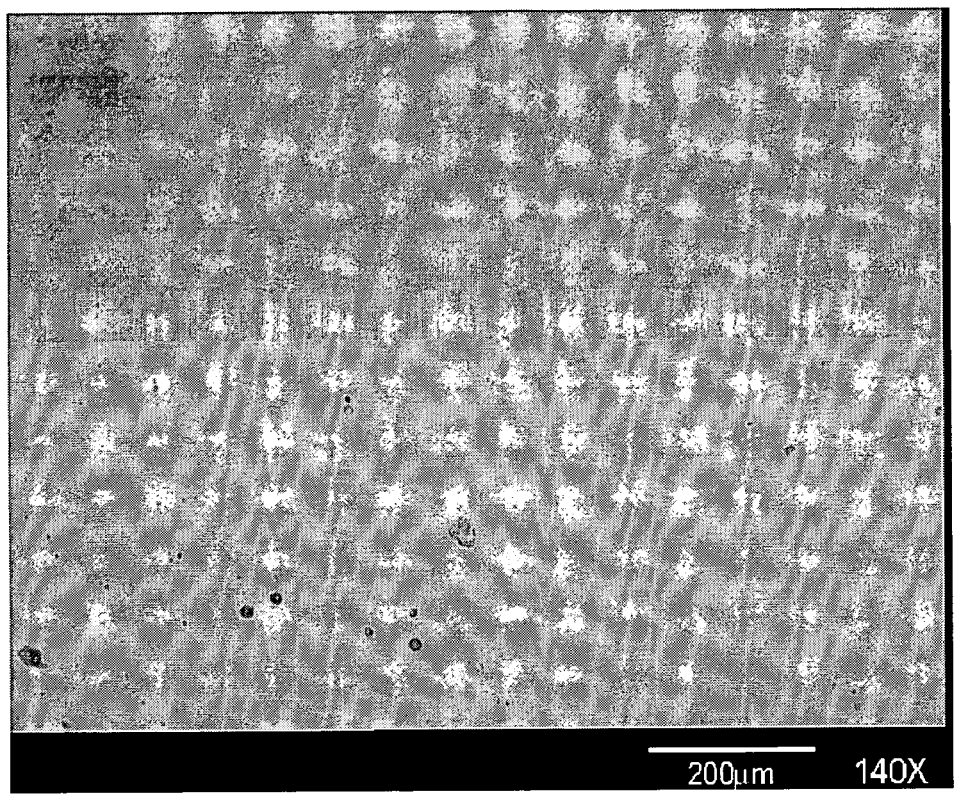
FIG. 1A shows etched PMMA posts of about 15 μm wide and about 75 μm high. The PMMA posts were etched using ICP-RIE with $O_2$ gas and a titanium hard mask. This figure indicates that high aspect ratio features with straight sidewalls in polymers using RIE may be obtained.

The present invention provides plasma etched polymers for use as substrates for a variety of biological and chemical assays known in the art such as microarray and nanoarray assays. As disclosed herein, reactive ion etching (RIE) of a variety of polymers generates physically and chemically altered surfaces that may be used to construct arrays for use in assays and separation technologies.

The reactive ion etched surfaces have binding affinities for chemicals and biomolecules that are different from unetched surfaces. The surfaces may be etched in desired patterns to immobilize given chemicals or biomolecules in a desired pattern. The etched and unetched regions may be arranged in a desired pattern using methods known in the art.

As used herein, "array" refers to a plurality of spatially arranged and immobilized specific binding agents that specifically interact with or bind to given analytes in an array format. The physical area covered by the specific binding agents may be readily modified and optimized by one skilled in the art.

As used herein, "affixed", "attached", "associated", "conjugated", "connected", "immobilized", "adsorbed", and "linked" are used interchangeably and encompass direct as well as indirect connection, attachment, linkage, or conjugation, which may be reversible or irreversible, unless the context clearly dictates otherwise.

As used herein, a "specific binding agent", "receptor", "capture agent" and "capture reagent" are used interchangeably to refer to an agent that specifically interacts with or binds to a ligand.

As used herein, a "ligand" is used interchangeably with an "analyte" and refers to an atom, molecule, or ion that binds or interacts with a given receptor to form a complex.

Depending on the chemistry, the receptor/ligand interaction may be reversible or irreversible. The extent of the binding depends on the affinity of the ligand to the receptor. In the presence of multiple ligands and receptors, the binding can be competitive (different ligands compete for the same receptor) or non-competitive (each ligand binds to a different receptor).

The specific binding agent can be immobilized on the substrate surface in a manner that provides for qualitative and/or quantitative determination of the analyte identity via interaction with the specific binding agent. See e.g. O'Brien, J., et al. (2000) Anal. Chem. 72:703, which is incorporated herein by reference. Receptors and ligands include biomolecules such as cellular receptors, peptides, polypeptides, proteins, antibodies, antigens, polynucleotides, polysaccharides, lipids, steroids, prostaglandins, prostacyclines, organic compounds, inorganic compounds, combinations thereof, and the like.

The reactive ion etched surfaces of the present invention may be used for medical applications such as assays for cancer, abnormal levels of certain biomolecules, abnormal biomolecules, specific nucleic acid sequences, specific antibodies, toxins, and the like, in a sample. The reactive ion etched surfaces of the present invention may be used for environmental applications such as assays for insecticides, pesticides, herbicides, toxins, bacteria, and the like, in food supplies or other environmental media, e.g., water and air. The reactive ion etched surfaces of the present invention may used to assay for chemical and biological agents that may be used in biochemical warfare such as organisms belonging to the genera *Bacillus, Mycobacterium, Francisella, Brucella, Clostridium, Yersinia, Variola, Orthopox,* and *Burkholderia*, viruses such as those that cause Congo-Crimean hemorrhagic fever (CCHF), Ebola Haemorrhagic Fever, Rift Valley Fever (RVF), smallpox, and Venezuelan equine encephalitis (VEE), toxins such as *Clostridium* neurotoxins, ricin toxin, saxitoxin, enterotoxins, exotoxins, mycotoxins, and the like, tabun, sarin, soman, methylphosphonothioic acid, sulphur mustard, nitrogen mustard, lewisite, phosgene oximine, phosgene, diphosgene, chloropicrin, organophosphates (OPs), pesticides, insecticides, and the like. Various known receptors or specific binding agents, such as nucleic acids based aptamers, affabodies, engineered peptides and antibodies, chemical capture reagents, evolved proteins or antibody based affinity reagents, polyclonal and monoclonal antibodies, and the like, that are known to specifically bind given analytes, such as the analytes referenced above may be used.

Due to the affinity of the reactive ion etched surfaces for solution-phase components, RIE treated polymeric surfaces may also be used in separation technologies such as field-flow-fractionation, thin layer chromatography, affinity chromatography using immobilized capture reagents, or similar chromatography applications commonly used to separate, isolate, filter, or purify a contaminant/ligand of interest from a sample.

Due to the ability to immobilize a specific binding agent on an RIE treated surface, specific binding agents immobilized on RIE treated surfaces may be used in devices for affinity purification processes known in the art, including biological manufacturing applications whereby a mixture of biomolecules is enriched by affinity chromatography in one component to the exclusion of the other components. Examples of this include affinity purification of a polyclonal antibody mixture with immobilized antigen to enrich the specific antigen binding component or protein-A/G chromatography that is commonly used to purify monoclonal antibodies from ascite fluid during production or manufacturing.

Thus, the present invention provides reactive ion etched surfaces that may be used in methods and devices for assaying or isolating at least one analyte in a fluid sample. In particular, the present invention provides methods and devices for assaying or isolating at least one ligand in a sample that specifically binds a specific binding agent that is immobilized on a reactive ion etched surface.

As used herein, "assaying" is used interchangeably with "detecting", "measuring", "monitoring" and "analyzing". As used herein, "separating", "isolating", "filtering", "affinity chromatography", and "purifying" are used interchangeably to indicate isolating a given agent from other agents.

As used herein, a "fluid sample" refers to a continuous amorphous substance that tends to flow and to conform to the outline of a container, such as a liquid or a gas. Fluid samples include blood, plasma, urine, bile, breast milk, semen, water, liquid beverages, air, and the like. If one desires to test a solid sample for a given analyte according to the present invention, the solid sample may be made into a fluid sample using methods known in the art. For example, a solid sample may be dissolved in an aqueous solution, ground up or liquefied, dispersed in a liquid medium, and the like. Alternatively, the surface of the solid sample may be tested by washing the surface with a solution such as water or a buffer and then testing the solution for the presence or absence of the given analyte.

As used herein, "specifically binds" refers to a specific binding agent's preferential interaction with a given ligand over other agents in a sample. For example, a specific binding agent that specifically binds a given ligand, binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art.

The assay devices according to the present invention are preferably made of materials that are suitable for micromachining or microfabrication, such as silicon, silica, quartz, glass, controlled pore glass, carbon, alumina, titania, tantalum oxide, germanium, silicon nitride, zeolites, gallium arsenide, gold, platinum, aluminum, copper and titanium, polymers, combinations thereof, and the like. The substrates upon which specific binding agents are immobilized thereon are preferably made of materials that are optically transparent. The substrates upon which the specific binding agents are immobilized thereon are preferably made of materials that do not substantially affect the assay and reagents in which the substrates of the present invention are employed. In preferred embodiments, the substrates comprise polymers such as polystyrene; poly(tetra)fluoroethylene (PTFE); polyvinylidenedifluoride; polycarbonate (PC); polymethylmethacrylate (PMMA); polyvinylethylene; polyethyleneimine; poly(etherether)ketone; polyoxymethylene (POM);

polyvinylphenol; polylactides; polymethacrylimide (PMI); polyetherimide (PEI), cyclo-olefin, polyalkenesulfone (PAS); polypropylene; polyethylene; polyhydroxyethylmethacrylate (HEMA); polydimethylsiloxane (PDMS); polyacrylamide; polyimide; and block-copolymers, and the like, and combinations thereof.

Although certain reactive ion etching methods and substrates are exemplified herein, other substrates, methods and devices for reactive ion etching known in the art may be used according to the present invention. See e.g. U.S. Patent Applications: 20040219790, 20040203242, 20040099631, 20040063317, 20030235994, 20030171000, 20030143870, 20030128463, 20030116532, 20030092276, 20030066816, 20020111031, 20020079054, 20020046986, and the like; and U.S. Pat. Nos. 6,786,978, 6,780,337, 6,689,698, 6,719,918, 6,669,807, 6,391,216, 6,295,986, 6,221,775, 6,028,394, 6,001,268, 5,705,411, 5,681,419, 5,578,166, 5,496,437, 5,395,741, 5,382,320, 5,304,278, 5,007,982, 4,826,564, 4,528,066, 4,478,678, 4,472,237, 4,444,617, 4,439,294, 4,343,677, 4,326,911, 4,229,233, 4,214,946, and the like; publications and books: PLASMA ETCHING AND REACTIVE ION ETCHING (American Vacuum Society monograph series) by Coburn, American Institute of Physics (1982); PLASMA ETCHING: AN INTRODUCTION (Plasma: Materials Interactions) by Manos & Flamm, Academic Press (1989), HANDBOOK OF PLASMA IMMERSION ION IMPLANTATION AND DEPOSITION by André Anders (Editor), Wiley-Interscience (2000), ETCHING IN MICROSYSTEM TECHNOLOGY by Michael Köhler Wiley-VCH (1999), HANDBOOK OF PLASMA PROCESSING TECHNOLOGY: FUNDAMENTALS, ETCHING, DEPOSITION, AND SURFACE INTERACTIONS (Materials Science and Process Technology) by Rossnagel, et al., Publications (1990), PLASMA ETCHING: FUNDAMENTALS AND APPLICATIONS (Series on Semiconductor Science and Technology, 7) by Sugawara, et al., Oxford University Press (1998), PLASMA DEPOSITION, TREATMENT, AND ETCHING OF POLYMERS: THE TREATMENT AND ETCHING OF POLYMERS (Plasma-Materials Interactions) by D'Agostino, Academic Press, (1990), and the semiannual conference proceedings of the Electrochemical Society on plasma processing, and the like, all of which are herein incorporated by reference.

The etched and unetched substrate surfaces of the present invention may be chemically modified to include functional moieties that may react with activated carboxylic acids or electron poor olefins, such as carboxylic acid groups, amine groups, sulfonic acid groups, and the like, using methods known in the art. See e.g. Lee, et al. (1996) Biomaterials 17:1599-1608; and Twaik, et al. (1969) J. Polym. Sci. 7:2469-2480, which are herein incorporated by reference. One skilled in the art may readily select and employ desired functional moieties to achieve desired properties including making the polymeric surfaces "super-resistant" to biofouling or non-specific adsorption or binding.

As exemplified herein, a low pressure oxygen plasma was used to anisotropically etch about 25 to about 30 µm deep features into polymethylmethacrylate (PMMA), polycarbonate (PC) and the cyclo-olefin, Zeonex® (Zeon Chemicals, Louisville, Ky.). Etched polymer surfaces were found to be roughened and more hydrophilic than unetched surfaces as based on water contact angle measurements and FT-IR analysis. As provided herein, specific binding agents, peptides and proteins, were found to selectively bind to etched PMMA and Zeonex® surfaces over unetched PMMA and Zeonex® surfaces. Conversely, the specific binding agents were found to selectively bind to unetched PC surfaces over etched PC surfaces. Thus, various polymer substrates may be etched to achieve differential molecule immobilization for construction of spatially complex, arrayed specific binding agents.

Also exemplified herein, antibodies were patterned on etched PMMA and Zeonex® surfaces and immunochemical assays for cholera toxin (CT) and *Staphylococcus* enterotoxin B (SEB) were successfully conducted. Thus, the reactive ion etched surfaces of the present invention may be employed in various assay devices and assays known in the art.

A. Reactive Ion Etching of Polymers

1. Reactive Ion Etching

Reactive ion etching (RIE) is accomplished with a reactive gas plasma to form volatile products and with energetic ion bombardment, i.e. the etch mechanism comprises both a chemical and a physical component Ion bombardment is necessary to achieve anisotropic etching but may induce physical damage to substrates. High ion fluxes generated with high density plasma RIE techniques enable high etch rates and anisotropy to be maintained with low ion bombardment energies, thereby mitigating substrate damage. While both ion density (flux) and ion energy are regulated by a single radio frequency (RF) power source in conventional RIE, high density plasma etching using an inductively-coupled plasma (ICP-RIE) allows ion density and ion bombardment energy to be separately controlled in order to achieve high etch rates with minimal physical damage to the substrate.

2. Polymer Etch Chemistries

Polymers are commonly etched in a pure oxygen plasma, which spontaneously reacts with the organic substrate to form volatile products without leaving a residue. Anisotropic profile control is achieved by etching at a low pressure and at low temperatures, which suppress spontaneous lateral etching of feature sidewalls. Other polymer etch chemistries include oxygen-fluorocarbon gas mixtures which typically increase the etch rate of organic materials, and oxygen-deficient oxygen-argon plasmas which produce graphitized sidewalls to improve anisotropy. One skilled in the art may readily select a plasma composition for obtaining desired characteristics of the etched surface, e.g. presence or absence of chemical moieties, such as inert fluorocarbon entities, carbonyl, hydroxyl and amine functionalities, and the like.

3. Polymer Selection

A series of candidate polymers, selected on the basis of chemical compatibility, biocompatibility, processability and optical properties, were studied to determine their suitability for protein microarray and microfluidic applications. It is noted, however, that one skilled in the art may readily select suitable polymers for desired applications, such as DNA or protein microarrays, using methods and knowledge in the art. The polymers exemplified herein are polymethylmethacrylate (PMMA), polycarbonate (PC), polyetherimide (PEI) and the cyclo-olefin, Zeonex®. Cell-cast Acrylite OP-1 PMMA sheets (1.0 mm thick) were purchased from Cyro Industries (Rockaway, N.J.). Calibre 301-06 PC sheets (1.0 mm thick) were obtained from Dow Chemical Co. (Midland, Mich.). PEI EI-3 sheets (1.6 mm thick) were purchased from Goodfellow Corp. (Berwyn, Pa.). Injection molded Zeonex® 480R plaques were obtained from Zeon Chemicals (Louisville, Ky.).

4. Substrate Fabrication 100 mm-diameter wafers (substrates) were machined from commercially available PMMA, PC, PEI and Zeonex® sheets using methods known in the art. The substrates were cleaned with methanol using lint-free cleanroom wipes and rinsed in deionized water, and then annealed at 110° C. for 24 hours. An electron-beam evaporator (CHA Industries, Redwood City, Calif.) was used to deposit about a 3000 to about a 4000 Å titanium hard mask layer (emission current=0.1 A, emission voltage=10 kV, deposition time=6 minutes) and about a 1 μm thick layer of OCG 825 positive photoresist (Arch Chemicals, Inc., Columbus, Ohio) was spin-coated (500 rpm for 5 seconds, 4600 rpm for 30 seconds) and baked (ramped up 1° C./min. to 90° C. for 25 minutes, ramped down 1° C./min. to 25° C.). After exposure, the photoresist was developed with OCG 934 developer (1 minute) and hard-baked (ramped up 1° C./min. to 90° C. for 30 minutes, ramped down 1° C./min. to 25° C.). The titanium mask was patterned by etching in a $CF_4$ plasma using methods known in the art.

5. RIE Experiments

All plasma etching was performed in an Oxford Plasmalab 100 ICP system (Oxford Instruments, Concord, Mass.) using methods known in the art. The ICP source was an induction coil powered through a matching network by a 13.56 MHz, 2000 W power supply. An electrostatic chuck allows the substrate to be RF biased using a variable RF power supply. Backside helium pressure ensures good thermal contact between the substrate and the liquid nitrogen-cooled chuck. $O_2$ plasma etching was carried out using methods known in the art under various conditions by changing ICP power, RF power, and wafer chuck temperature.

Initial RIE process parameters of $O_2$=100 sccm, ICP Power=500 W, RF Power=300 W (DC bias=320 V) and temperature=10° C. were used and resulted in bulk wafer deformation and mask delamination due to excessive heating of the substrate. The temperature of the chuck and the ICP and RF powers were then lowered to 0° C., 300 W and 100 W (DC bias about 320 V), respectively. Although no bulk distortion of the polymer substrate was observed, edge deformation of etched PMMA features was observed at 50× magnification. Lowering the temperature of the wafer chuck to −10° C. mitigated thermal distortion of the polymer substrate.

6. Polymer RIE Process Optimization

In order to improve etch rates and decrease substrate damage, three variables, ICP power, RF power, and temperature, were optimized. PMMA was used as the polymer substrate for RIE process optimization. Process parameters were optimized to yield vertical etch profiles and straight sidewalls with minimal thermal damage to polymer substrates. A low pressure of 10 mT was used to achieve directional etching and to minimize feature undercutting. For materials with poor thermal conductivity, such as polymers, temperature control may be improved by allowing the substrate to cool using backside helium flow while clamped on the liquid nitrogen-cooled wafer chuck for at least a few minutes prior to processing.

Initial RIE process parameters of $O_2$=100 sccm, ICP Power=500 W, RF Power=300 W (DC bias=320 V) and temperature=10° C. were used and resulted in bulk wafer deformation and mask delamination due to excessive heating of the substrate. The temperature of the chuck and the ICP and RF powers were lowered to 0° C., 300 W and 100 W (DC bias about 320 V), respectively. Although no bulk distortion of the polymer substrate was observed, edge deformation of etched PMMA features was observed at 50× magnification. Lowering the temperature of the wafer chuck to −10° C. mitigated thermal distortion of the polymer substrate.

Figure 1B:
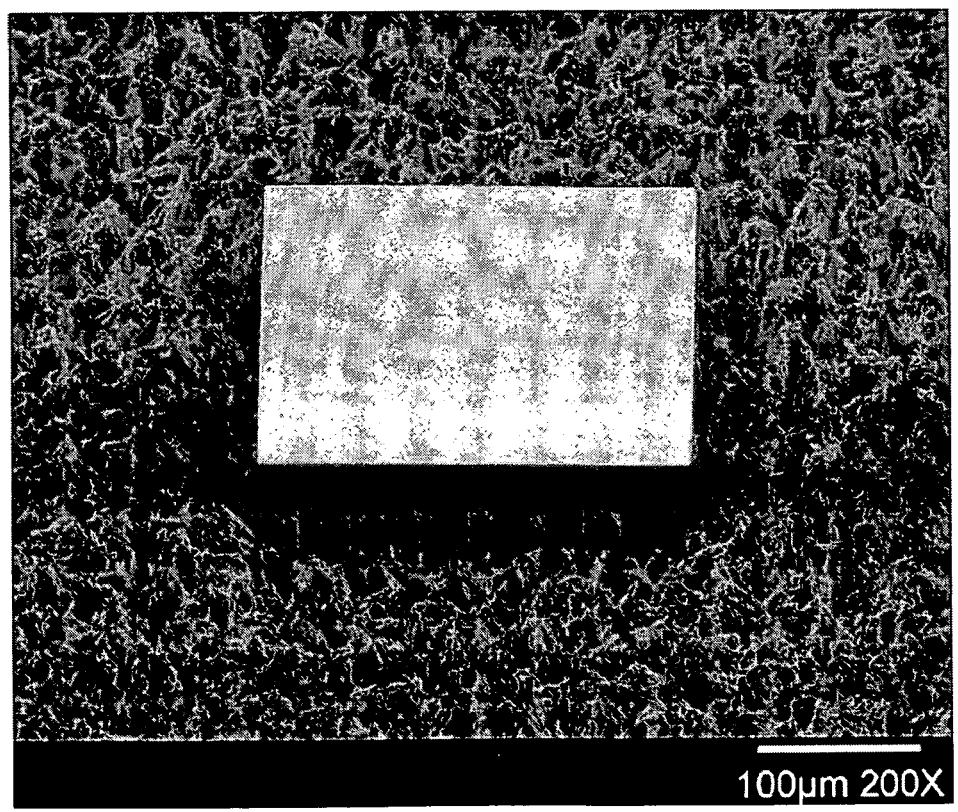
FIG. 1B is a SEM micrograph of an etched PMMA substrate about 75 μm high showing significant surface and sidewall roughening results from ICP-RIE with $O_2$ gas.

After 2 hours, roughening of the bottom surface of etched features was observed under magnification. Both narrow and wide features were etched to depths of about 75 μm, resulting in about a 0.60 μm/min. etch rate. Vertical feature profiles and aspect ratios of up to about 5:1 were achieved as shown in FIG. 1A. Roughened feature sidewalls and bottom surfaces result from this RIE process, as shown by SEM microscopy. See FIG. 1B. Micromasking by sputtered metal from the etch mask is often attributed as the likely cause of grass-like surface roughness. A PMMA substrate etched using a photoresist etch mask also exhibited significant roughness (data not shown).

7. Effect of Polymer Structure on RIE

Patterned PMMA, PC, PEI and Zeonex® substrates were etched to depths of about 40 to about 50 μm using the following RIE process parameters:

| | |
|---|---|
| $O_2$ | 100 sccm |
| Pressure | 10 mT |
| ICP Power | 300 W |
| RF Power | 100 W (DC bias ≈ 328 V) |
| Temperature | −10° C. |
| Backside He | 4 T |

Etch resistance is dependent on the polymer structure. Etch rates for PMMA, PC, PEI and Zeonex® were about 0.60, 0.25, 0.18 and 0.18 μm/min., respectively. The high etch resistance exhibited by PEI may be attributed to the high degree of aromaticity in its structure, while the etch resistance exhibited by Zeonex® could be due to the absence of oxygen-containing functional groups that are particularly susceptible to degradation under oxygen plasma. Oxygen-containing functional groups are present in the structures of both PMMA and PC, but PC has an aromatic structure that probably renders it more etch resistant than PMMA. The presence of cross-linkers in PMMA may also accelerate degradation under oxygen plasma treatment. These characteristics may be used in order to obtain desired results. For example, in order to reduce array fabrication time, one may select substrates that undergo faster degradation. Alternatively, in order create arrays having etch resistant areas or surfaces, one may select substrates that lack oxygen-containing functional groups or contain aromatic structures.

B. Patterning of Specific Binding Agents

Reactive ion etching of a variety of polymers generates high aspect ratio features with significant surface roughness. As provided herein, the reactive ion etched surfaces of the present invention may be used to enhance immobilization or concentrations of specific binding agents on polymer surfaces. The reactive ion etched surfaces may be used to provide patterned arrays.

The methods disclosed herein may be used, alone or in combination, with other patterning methods known in the art including photolithography, microcontact printing, nanografting, and spot arraying. See e.g. U.S. Patent Application Publications: 20030068446, 20020084429, 20020123227, 20030059537, 20030153010, 20040053354, 20040213910, and the like; U.S. Pat. Nos. 6,776,094, 6,579,673, 6,579,463, 6,541,022, 6,518,194, 6,444,254, 6,180,239, 5,965,305, 5,847,019, 5,773,308, 5,622,826, and the like; Publications and books: INTRODUCTION TO BIOPHOTONICS by Paras N. Prasad Wiley-Interscience (2003), PROTEIN Microarray Technology by Dev Kambhampati (Editor) John Wiley & Sons (2004), Bioconjugation Protocols: Strategies and Methods (Methods in Molecular Biology (Clifton, N.J.), V. 283.) by Christof M. Niemeyer, John M. Walker Humana Press; (2004), DNA Microarrays and Gene Expression: From Experiments to Data Analysis and Modeling by Pierre Baldi, G. Wesley Hatfield, Wesley G. Hatfield Cambridge University Press (2002), Nanobiotechnology: Concepts, Applications and Perspectives by Christof M. Niemeyer (Editor), Chad A. Mirkin (Editor) John Wiley & Sons (2004), and Blaws & Reichert (1998) *Protein Patterning, Biomaterials* 19:595-609, and the like, all of which are herein incorporated by reference.

1. Fabrication of RIE-Patterned Polymer Substrates

Polymer slides (about 25 mm×about 75 mm) were cut from commercially available PMMA, PC, and Zeonex® sheets. PEI was not used as a substrate for patterning experiments because of background fluorescence. However, it is noted that use of intrinsically fluorescent substrates, such as PEI, may be desired in some applications such as assays wherein the fluorescence of PEI may be modulated by or employed in the detection sequence for determining the presence of a ligand captured at the surface.

The substrates were cleaned with methanol using lint-free cleanroom wipes. About 25 to about 30 μm deep, 1.5 mm diameter holes were etched in an array using a stainless steel stencil mask obtained from Kimball Physics (Wilton, N.H.). The RIE process parameters used were: $O_2$=100 sccm, ICP Power=300 W, RF Power=100 W (DC bias=328 V) and temperature=-10° C.

2A. Patterning Experiments

All polyclonal antibodies (either mouse α-goat or goat α-mouse antibody commercially available with a Cy3 fluorescent label) were purchased from Zymed, Inc. (South San Francisco, Calif.) and were supplied as 1 mg/ml solutions supplemented with 10 mg/ml BSA and used as provided unless indicated otherwise. Polyclonal immunoglobulin (IgG) solution was applied in 50 μl volumes and allowed to incubate with the surface for about 2 to about 3 hours. Post-incubation, the surface was liberally washed with phosphate buffered saline (PBS, pH 7.4) supplemented with 0.1% of the detergent Tween-20 (PBST). Subsequent to washing away the buffer in deionized water, the polymer was air dried for imaging.

Imaging was performed using the 532 nm excitation source of an Axon Instruments (Union City, Calif.) microarray scanner. A typical PMT setting was about 700 or greater with laser power at about 33%. Pixel size was set to 40 μm/pixel. Data from experiments was quantified by densitometry, and a comparison of fluorescence intensity on the RIE treated surface vs. the native polymer surface provides a measure of the differential affinity of the antibody for the treated surface over that of the bulk, native polymer. See Suh, K. Y., et al. (2004) Biomaterials 25:557-563, which is herein incorporated by reference.

2B. Patterning Results

It was found that polyclonal IgG binds differentially to etched and unetched regions of reactive ion etched surfaces. In the case of PMMA and Zeonex®, the fluorescently labeled IgG selectively bound to etched areas (FIGS. 2A and 2B, respectively), whereas for PC, the protein localizes in the native, unetched regions (FIG. 2C).

Thus, the reactive ion etched surfaces of the present invention may be used to immobilize specific binding agents for use in assays without the need for non-specific blocking buffers or other means and methods to enhance signal-to-noise ratios by preventing undesired agents from being localized on undesired areas. For example, if a specific binding agent is to be immobilized on a desired surface of PMMA or Zeonex®, the desired surface would be reactive ion etched and the undesired surface would remain unetched. When the specific binding agent is contacted with the etched and unetched surfaces, the specific binding agent would localize on or adsorb onto the etched surfaces, but not the unetched surfaces. If a specific binding agent is to be immobilized on a desired surface of PC, the desired surface would remain unetched, and the undesired surface would be etched. It should be noted that specific binding agents may have different affinities for various etched and unetched polymers. However, based on the disclosure herein and methods known in the art, one skilled in the art may readily select, without undue experimentation, combinations of etched and unetched polymers and specific binding agents that are suitable for a desired application.

It should be noted that a plurality of polymers having surfaces that are etched and unetched and different specific binding agents may be selected to provide various combinations resulting in arrays having selective patterning of specific binding agents. For example, a substrate may comprise two polymers as a block polymer, such as PMMA and PC. PMMA and PC may be in a given pattern to provide a patterned surface of the different polymers, such as a checkerboard pattern. Part of the PMMA surfaces may be reactive ion etched while the other part remains unetched. Likewise, part of the PC surfaces may be reactive ion etched while the other part remains unetched. A first specific binding agent may only adsorb to etched PMMA surfaces. A second specific binding agent may only adsorb to unetched PMMA surfaces. A third specific binding agent may only adsorb to unetched PC surfaces. The substrate with the specific binding agents immobilized thereon may be used to simultaneously assay for at least three different analytes.

3. Concentration Dependence of the Specific Binding Agent-Surface Interaction

Figure 3A:
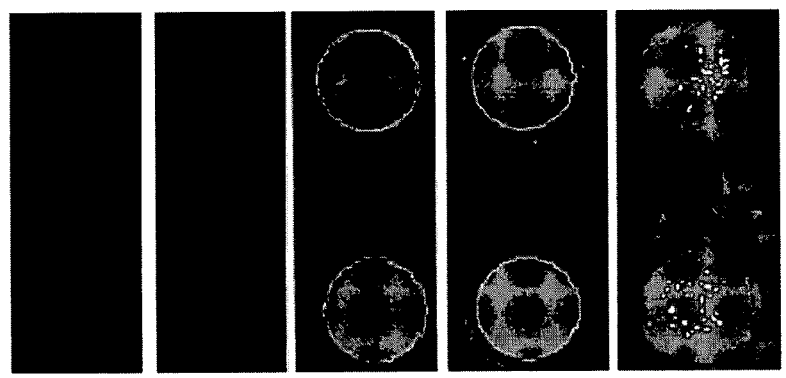
FIG. 3A shows IgG-Cy3 antibody (about 1 mg/ml) was applied to a PMMA substrate at concentrations of about 1 mg/ml, about 0.1 mg/ml, about 0.01 mg/ml, about $1 \times 10^{-3}$ mg/ml, and about $1 \times 10^{-4}$ mg/ml.
Figure 3B:
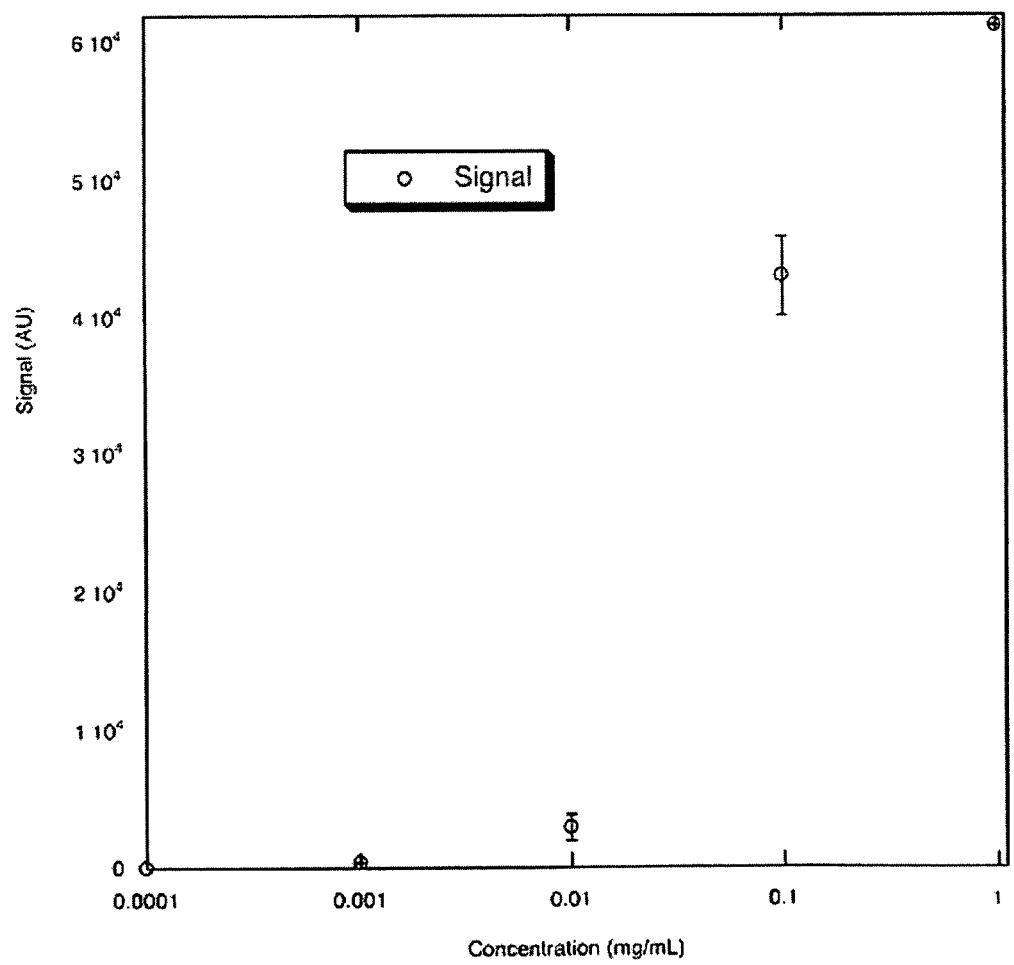
FIG. 3B shows protein adsorption is dependent on the concentration of protein applied to the surface.

To examine the concentration dependence for the interaction between the specific binding agent and a RIE-patterned PMMA surface, polyclonal IgG was applied at concentrations of about 1 mg/ml, about 0.1 mg/ml, about 0.01 mg/ml, about $1 \times 10^{-3}$ mg/ml, and about $1 \times 10^{-4}$ mg/ml in phosphate buffered saline (PBS, pH 7.4) supplemented with 0.1% (v/v) TWEEN-20 (polysorbate 20) and allowed to incubate for 2 hours. Subsequent washing with PBST to remove unbound antibody, rinsing with deionized water, and drying of the polymer allowed for imaging (as described) that resulted in data suitable for quantification and graphical analysis. FIG. 3 demonstrates that protein adsorption is dependent on the concentration of protein applied to the surface. The curve approximates a Langmuir binding isotherm for surface adsorption as known in the art.

C. Assays

As provided herein, the patterned, reactive ion etched surfaces may be used to selectively immobilize specific binding agents in order to assay for given analytes. The etched surfaces, according to the present invention, obviate the need for polysaccharide, ethanolamine, 2-thiolethanol, poly(ethylene) glycol, or proteinacous, such as bovine serum albumin, based blocking protocols that are currently used to minimize non-specific binding, such as the undersired, non-specific binding of fluorescent antigen from solution to glass-based microarray surfaces. As provided herein, immunochemical assays for the detection of fluorescently labeled cholera toxin and *Staphylococcus* enterotoxin B is exemplified. The cholera toxin immunoassay was performed with a BSA blocking step while the *Staphylococcus* enterotoxin B was performed without BSA. Again, it should be noted, that other specific binding agents and assays known in the art may be employed according to the present invention.

1. Immunoassay Experiments

All immobilizations on polymeric surfaces and immunochemical assays were performed in phosphate buffered saline (PBS, pH 7.4) supplemented with the detergent Tween-20.

Monoclonal α-cholera toxin was purchased from Biodesign (Saco, Me.) as a concentrated solution that was diluted to 1 mg/ml and stored at −20° C. in 40% glycerol/60% PBS buffer for use as required. Rhodamine labeled β-subunit of cholera toxin was purchased from ListLabs, Inc. (Campbell, Calif.). *B. anthracis* protective antigen (EMD Biosciences, San Diego, Calif.) was labeled with ALEXAFLUOR (dye) 532 and purified as per the manufacturer's instructions (Molecular Probes, Eugene, Oreg.). α-cholera toxin was incubated for 2 hours on a patterned ZEONEX (cyclo-olefin) substrate and washed off with 0.1% (w/v) PBST. Application of 1% (w/v) BSA as a blocking agent to the entire polymeric surface (RIE treated and non-RIE treated) minimized non-specific binding of fluorescent antigen to the polymeric surfaces in subsequent manipulations. After 1 hour, BSA was removed and either fluorescently labeled cholera toxin or *B. anthracis* protective antigen was added to the patterned antibodies and allowed to incubate for 1 hour. Excess antigen was removed, the surface was liberally washed with PBST, rinsed with Milli-Q water, air dried, and imaged.

In another immunochemical assay, α-*Staphylococcus* enterotoxin B monoclonal antibodies (Mab) (Sigma-Aldrich, Co., St. Louis, Mo.) were applied as 50 µl of 1 mg/ml solution (0.1% (w/v) PBST supplemented with 1 mg/ml BSA) to two different sections of RIE patterned PMMA. After a 2 hour incubation, the Mab containing solution was removed, the surface washed with 0.1% (w/v) PBST, and either *Staphylococcus* enterotoxin B or diphtheria toxin (ListLabs, Inc., Campbell, Calif.) labeled with AlexaFluor® 532 was added at 10 µg/ml. After a 1 hour incubation, the solution was removed, the surface washed with 0.1% (w/v) PBST, and the slide imaged as described above. No BSA blocking of free polymer surface was performed in this experiment.

2. Immunoassay Results

FIG. 4 shows that for the etched polymer surface patterned with anti-cholera toxin antibody (α-CT), fluorescence was observed only where fluorescently labeled cholera toxin (CT) was applied. Application of a solution of fluorescently labeled protective antigen (PA) resulted in little or no fluorescence because given the specificity of the antibody/antigen interaction, α-CT should not significantly bind PA. As per this description of differential protein interaction between the RIE treated and native polymeric surface (FIGS. 1-3), and ensured by the inclusion of an additional BSA blocking step, there should be no free area available for non-specific interaction between the fluorescently labeled protein and the polymer surface, which was observed.

Similarly, FIG. 5 demonstrates that for the PMMA surface patterned with α-*Staphylococcus* enterotoxin B (α-SEB), fluorescence was observed only where fluorescently labeled SEB was applied, while no localized fluorescence was observed upon the addition of fluorescently labeled diphtheria toxin (DT).

These experiments demonstrate that adding a bulk antibody solution to RIE-patterned PMMA and ZEONEX (cyclo-olefin) surfaces results in functional antibodies bound only to the reactive ion etched surfaces. As noted above, specific binding agents localized on unetched surfaces of PC. Thus, use of substrates containing reactive ion etched surfaces and unetched surfaces in assays eliminates the need for blocking protocols since given specific binding agents are immobilized on given etched surfaces and given unetched surfaces, thereby resulting in areas that are essentially blocked.

D. Surface Characterization

Several surface analysis techniques were employed to chemically and physically characterize the etched polymers in order to elucidate the mechanism of protein adsorption on RIE-treated polymer surfaces.

1. Scanning Electron Microscopy (SEM)

SEM images were captured on a field emission scanning electron microscope, JEOL 6400F, with about a 2 to about a 4 kV beam from graphite-coated samples. The surfaces of about 25 to about 30 µm deep etched holes in PMMA, Zeonex® and PC substrates were significantly roughened, as shown in FIGS. 6A, 6B and 6C, respectively. Increased roughness of the etched surfaces results in increased surface area and increased three-dimensional structures that are believed to increase immobilization and concentrations of specific binding agents.

2. Atomic Force Microscopy (AFM)

The etched holes on RIE patterned polymer substrates were examined with a NanoScope III AFM instrument (Veeco Instruments, Inc., Woodbury, N.Y.) in tapping mode. Roughness analyses of the AFM images (not shown) yielded root mean square (rms) roughness values of about 1.18 µm, about 1.09 µm, and about 0.77 µm for etched PMMA, Zeonex® and PC, respectively. Etched PMMA or Zeonex® exhibit more surface roughness than etched PC, which may partly account for differences in their protein adsorption behavior.

The rms roughness values indicate that etched PC exhibits less roughness than either etched PMMA or etched Zeonex®, which may account for the different protein adsorption behavior observed on the different substrates. However, it is important to note that in addition to this physical characteristic, chemical properties such as enhanced hydrophilicity may play a role in increased protein adsorption on the polymer surfaces as described herein.

3. Contact Angle Measurements

Contact angle measurements were conducted utilizing a Kruss (Kruss USA, Matthews, N.C.) G40 Contact Angle Measuring System. Doubly distilled water was used as the measured medium. Unetched surfaces were cleaned with both acetone and isopropanol rinses and dried with nitrogen before measurements were taken. Etched surfaces were not treated before measurements were taken. Droplets were introduced to the polymer surface through a manual microsyringe. Digital snapshots were taken of the droplets on the surface and analyzed with software provided by Kruss. Five replicates for each measurement were conducted to establish statistical significance.

Contact angle measurements for etched and unetched PMMA, Zeonex® and PC are presented in Table 1. The oxygen plasma etched polymer surfaces are significantly more hydrophilic than untreated surfaces, indicating that RIE generates polar groups that increase the surface energy of the polymer to enable enhanced wetting. Changes in contact angle over time were observed. This aging effect can be attributed to polymer chain motion reorienting the polar groups into the bulk. It should be noted though that after 20 days in air, the etched polymer surfaces remain more hydrophilic than the unetched surfaces.

TABLE 1

Water contact angle measurements for etched and unetched polymers

|  | PMMA | Zeonex® | PC |
| --- | --- | --- | --- |
| Unetched | 85.3° (+/−1.7) | 91.7° (+/−0.6) | 85.3° (+/−2.3) |
| Etched - 1 day after RIE | 30.6° (+/−3.5) | Droplet wets out immediately | Droplet wets out immediately |
| Etched - 20 days after RIE | 29.0° (+/−3.2) | 63.7° (+/−0.1) | 31.4° (+/−0.6) |

The increased hydrophilicity may contribute to enhanced penetration of solution into the interstices of the polymeric network produced by RIE treatment. The ability to significantly "wet" the surface with solvent, either through decreased water surface tension or other effects of the sort, may allow a greater surface area for the interaction between solvated molecules and polymer surface to occur. The increased likelihood of this interaction may allow for an increased propensity for phase-change to occur and the molecule to become desolvated onto the polymer surface.

4. Fourier Transform Infrared Spectroscopy (FTIR)

IR spectra of etched and unetched (control) polymer surfaces were collected on a Digilab FTS-7000 (Randolph, Mass.) using Harrick Scientific's Horizon, a horizontal attenuated total reflection (ATR) accessory (Ossining, N.Y.) with a ZnSe ATR crystal. For each spectrum 64 scans with 4 $cm^{-1}$ resolution were averaged.

Figure 7A:
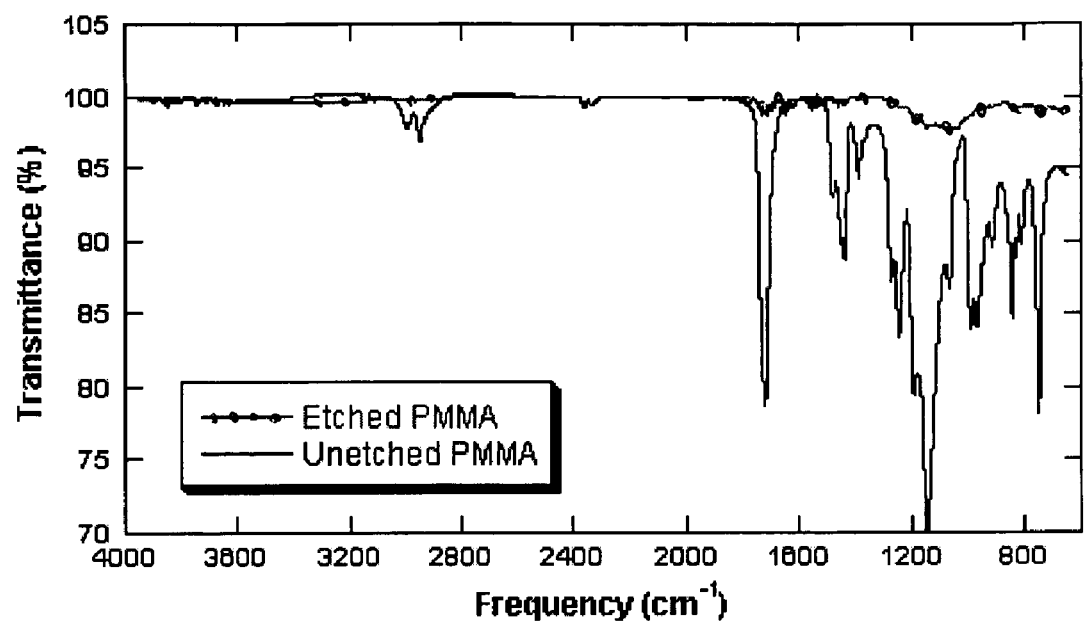
FIG. 7A shows an FTIR spectrum of etched and unetched PMMA.
Figure 7B:
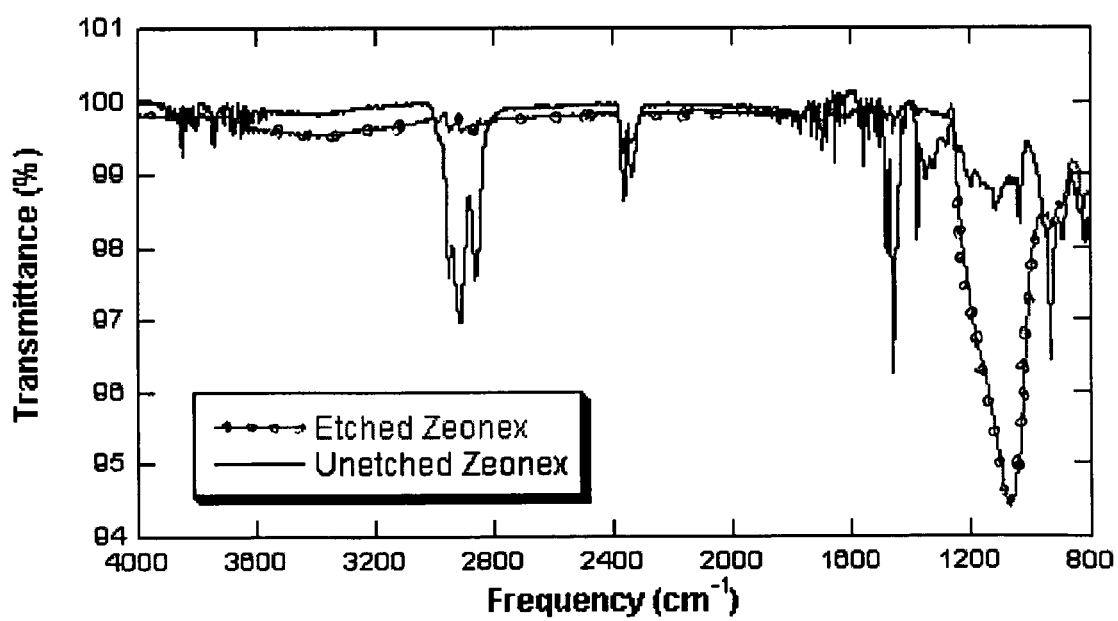
FIG. 7B shows an FTIR spectrum of etched and unetched Zeonex®.
Figure 7C:
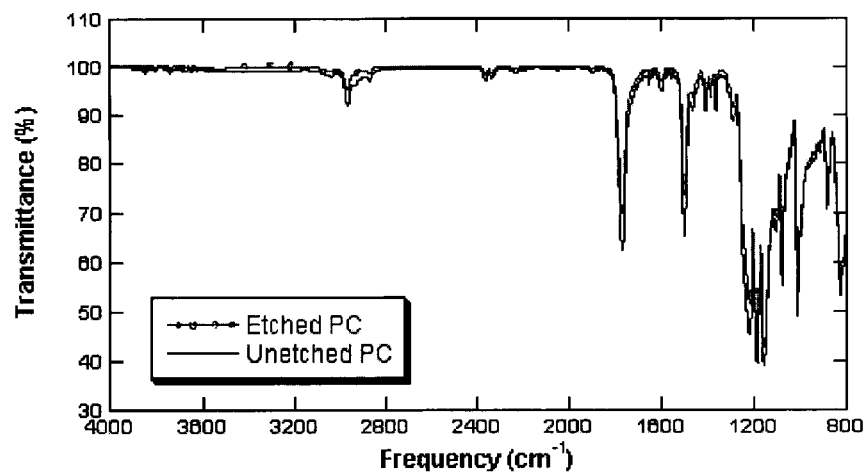
FIG. 7C shows an FTIR spectrum of etched and unetched PC.

FTIR spectra indicate that etching dramatically alters the chemical composition of PMMA and Zeonex® surfaces. See FIGS. 7A and 7B, respectively. No chemical differences between etched and unetched PC were detected with this technique. See FIG. 7C. Oxygen plasma treatments on polymer surfaces reportedly give rise to a number of incorporated hydrophilic moieties, such as carboxyl, carbonyl and ether functionalities. No IR absorption at about 1630 to about 1780 $cm^{-1}$ was observed for etched PMMA or Zeonex®, thereby indicating the absence of carbonyl-containing functionalities on these surfaces. Both etched PMMA and Zeonex® exhibited a broad absorption feature in the range of about 1050 to about 1150 $cm^{-1}$. Since contact angle measurements indicate that etching increases hydrophilicity, which in turn suggests the presence of polar oxygen-containing functional groups, this absorption likely corresponds to the carbon-oxygen single bond stretch of ether functionalities. In addition, the broad IR absorption in the range of about 3200 to about 3600 $cm^{-1}$ indicates the presence of adsorbed water on the etched PMMA and Zeonex® surfaces.

In conjunction with the observation of decreased contact angle as noted above, the FTIR results indicate an increased hydrophilicity as exhibited by the deposition of ambient moisture onto the surface of the RIE treated polymeric surface. Combined with the supposition of increased surface area, and potentially porosity, due to RIE treatment, this additional evidence for increased hydrophilicity of the polymeric surface implies that adsorption may be increased by the presence of a more "water-like" polymeric surface conducive to formation of biomolecule-polymer interactions that are energetically favorable for desolation.

E. Assay Device

Figure 8:
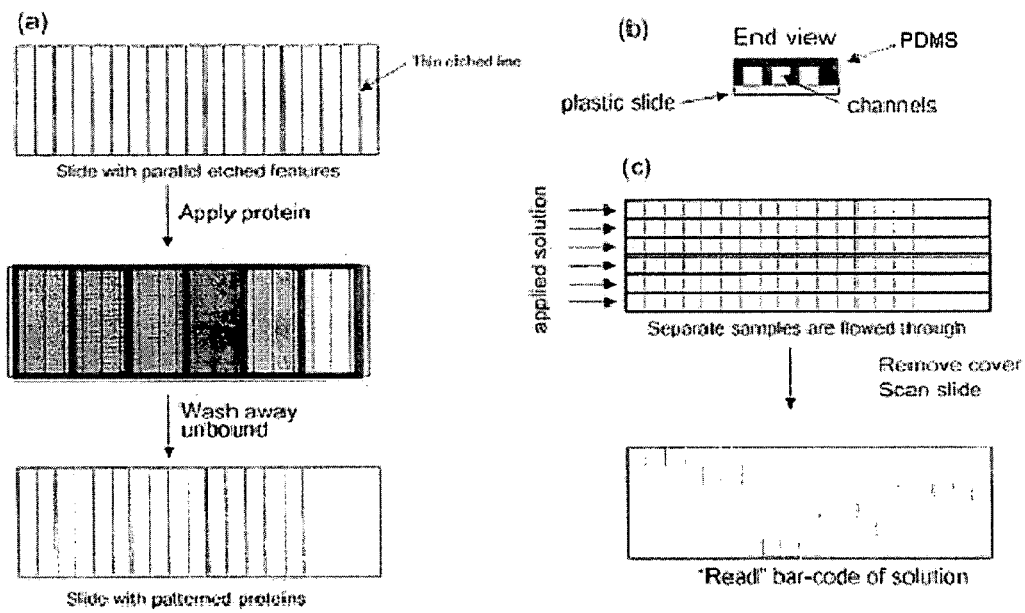
FIG. 8 shows an exemplary design and schematic of a device of the present invention.

FIG. 8 shows an exemplary design and schematic of a device of the present invention. (a) A polymeric substrate is etched to generate etched parallel lines. A solution of specific binding agents is applied to the etched parallel lines. Unbound specific binding agents are washed off, thereby resulting in a reactive ion etched substrate having patterned specific binding agents immobilized thereon. (b) A housing having microchannels, such as a PDMS cover, is placed orthogonal to the direction of the etched parallel lines. (c) At least one solution containing at least one ligand is flowed through the microchannels. Complexes of the specific binding agents and ligands may be detected using methods known in the art. Once the binding affinities of given ligands has been characterized, thereby resulting in a "bar-code" or fingerprint, the bar-code may be used to identify the ligands in unknown samples.

The examples provided herein are intended to illustrate but not to limit the invention.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A substrate comprising
   at least one reactive ion etched polymethylmethacrylate or cyclo-olefin surface having at least one polypeptide bound directly thereon;
   at least one unetched polymethylmethacrylate or cyclo-olefin surface which fails to bind the polypeptide directly thereon when contacted therewith; and
   at least one reactive ion etched or unetched surface of a second polymer wherein the reactive ion etched surface of the second polymer fails to bind the polypeptide directly thereon when contacted therewith;
   wherein the polypeptide specifically binds a ligand of interest in a sample to be assayed; and wherein said binding directly thereon is in the absence of a linker.

2. The substrate of claim 1, wherein at least one of the polymethylmethyacrylate or cyclo-olefin surfaces is adjacent to at least one of the surfaces of the second polymer.

3. The substrate of claim 1, wherein the polypeptide is an antigen or an antibody.

4. The substrate of claim 1, wherein the second polymer is polycarbonate.

5. The substrate of claim 1, wherein the unetched surface of the second polymer has a second polypeptide bound directly thereon which second polypeptide is the same as or different from the polypeptide bound directly thereon the reactive ion etched polymethylmethacrylate or cyclo-olefin surface.

6. The substrate of claim 1, wherein the reactive ion etched polymethylmethacrylate or cyclo-olefin surface is in a pattern on the substrate.

7. The substrate of claim 1, wherein the unetched surface is in a pattern on the substrate.

8. The substrate of claim 1, wherein the first and second polymers are in a pattern.

9. The substrate of claim 1, wherein the polypeptide is bound to the reactive ion etched polymethylmethacrylate or cyclo-olefin surface in the absence of a non-specific blocking buffer.

10. An assay device comprising the substrate of claim 1 operably attached to a housing.

11. A method of assaying or isolating a ligand in a sample which comprises contacting the substrate of claim 1 with the sample.

12. The method of claim 11, which further comprises detecting or measuring the polypeptide complexed with the ligand or the ligand complexed with the polypeptide.

13. A kit comprising the substrate of claim 1 packaged together with reagents for assaying or isolating the ligand.

* * * * *